United States Patent
Sankaran et al.

(10) Patent No.: US 10,354,349 B2
(45) Date of Patent: Jul. 16, 2019

(54) SYSTEMS AND METHODS FOR USING GEOMETRY SENSITIVITY INFORMATION FOR GUIDING WORKFLOW

(71) Applicant: HeartFlow, Inc., Redwood City, CA (US)

(72) Inventors: Sethuraman Sankaran, Palo Alto, CA (US); Leo J. Grady, Millbrae, CA (US); Charles A. Taylor, San Mateo, CA (US)

(73) Assignee: HeartFlow, Inc., Redwood City, CA (US)

(*) Notice: Subject to any disclaimer, the term of this patent is extended or adjusted under 35 U.S.C. 154(b) by 704 days.

(21) Appl. No.: 14/231,870

(22) Filed: Apr. 1, 2014

(65) Prior Publication Data
US 2015/0278976 A1    Oct. 1, 2015

(51) Int. Cl.
*G06Q 10/06*    (2012.01)
*G06Q 50/24*    (2012.01)
*G06Q 50/26*    (2012.01)

(52) U.S. Cl.
CPC ....... *G06Q 50/265* (2013.01); *G06Q 10/0633* (2013.01); *G06Q 50/24* (2013.01)

(58) Field of Classification Search
None
See application file for complete search history.

(56) References Cited

U.S. PATENT DOCUMENTS

| | | | |
|---|---|---|---|
| 7,458,936 | B2 | 12/2008 | Zhou |
| 8,315,812 | B2 | 11/2012 | Taylor |
| 8,812,355 | B2 | 8/2014 | Angell et al. |
| 2004/0047497 | A1* | 3/2004 | Daw et al. ............ 382/128 |
| 2004/0193036 | A1 | 9/2004 | Zhou |
| 2005/0075905 | A1 | 4/2005 | Bennett |
| 2008/0015910 | A1 | 1/2008 | Reisz et al. |
| 2009/0005693 | A1* | 1/2009 | Brauner et al. ........ 600/481 |
| 2009/0089107 | A1 | 4/2009 | Angell et al. |
| 2009/0125840 | A1 | 5/2009 | Squilla |
| 2010/0036254 | A1 | 2/2010 | Owsley et al. |

(Continued)

FOREIGN PATENT DOCUMENTS

| | | |
|---|---|---|
| EP | 1187070 A2 | 3/2002 |
| WO | WO 02/39899 A2 | 5/2002 |

OTHER PUBLICATIONS

U.S. Appl. No. 13/864,996, "Method and System for Sensitivity Analysis in Modeling Blood flow Characteristics," filed Apr. 17, 2013.

(Continued)

*Primary Examiner* — Elaine Gort
*Assistant Examiner* — Rachelle L Reichert
(74) *Attorney, Agent, or Firm* — Bookoff McAndrews, PLLC

(57) ABSTRACT

Systems and methods are disclosed for using geometry sensitivity information for guiding workflows in order to produce reliable models and quantities of interest. One method includes determining a geometric model associated with a target object; determining one or more quantities of interest; determining sensitivity information associated with one or more subdivisions of the geometric model and the one or more quantities of interest; and generating, using a processor, a workflow based on the sensitivity information.

17 Claims, 11 Drawing Sheets

(56) References Cited

U.S. PATENT DOCUMENTS

| | | |
|---|---|---|
| 2012/0041301 A1 | 2/2012 | Redel |
| 2012/0041323 A1 | 2/2012 | Taylor |
| 2012/0072190 A1 | 3/2012 | Sharma et al. |
| 2012/0203530 A1 | 8/2012 | Sharma et al. |
| 2013/0129165 A1 | 5/2013 | Dekel et al. |
| 2013/0132054 A1 | 5/2013 | Sharma et al. |
| 2013/0251219 A1 | 9/2013 | Mehta |
| 2014/0249784 A1 | 9/2014 | Sankaran et al. |
| 2014/0275947 A1 | 9/2014 | Fonte et al. |

OTHER PUBLICATIONS

U.S. Appl. No. 61/948,325, "Method and System for Geometric Sensitivity Prediction Using Machine Learning" filed Mar. 5, 2014.

Dibyendu Sengupta, 2013, "Risk Assessment Using Image-Based Hemodynamic Modeling of Patients With Coronary Artery Aneurysms Caused by Kawasaki Disease"; Ph.D. Dissertation. University of California at San Diego, La Jolla, CA, USA. Advisor(s) Alison L. Marsden. AA13564675. p. 1-126.

Sankaran S, Esmally Moghadam M, Kahn AM, Tseng EE, Guccione JM, Marsden AL.; "Patient-Specific Multiscale Modeling of Blood Flow for Coronary Artery Bypass Graft Surgery"; Ann Biomed Eng. Oct. 2012;40(10):2228-42. doI: 10.1007/s10439-012-0579-3. Epub Apr. 27, 2012. p. 2228-2242.

International Search Report and Written Opinion for corresponding Application No. PCT/US2015/022945 dated Jul. 15, 2015 (9 pages).

\* cited by examiner

SYSTEMS AND METHODS FOR USING GEOMETRY SENSITIVITY INFORMATION FOR GUIDING WORKFLOW

FIELD OF THE INVENTION

Various embodiments of the present disclosure relate generally to medical imaging and related methods. More specifically, particular embodiments of the present disclosure relate to systems and methods for using sensitivity information for guiding workflow.

BACKGROUND

Workflows are tools used to guide any process from start to finish in an organized, predictable fashion. Ideal workflows enhance efficiency while drawing attention to possible areas that may require scrutiny. In general, a workflow is comprised of a series of connected steps, typically automated or semi-automated and processed in sequence. Outputs and/or a subset of outputs from previous steps may be used as inputs in subsequent steps such that each step builds on previous steps. A guided workflow may be comprised of a semi-automated process where manual corrections may be made to the workflow and a sub-sequence of the workflow may be reprocessed. Intrusion (e.g., guiding a workflow) may be triggered, for example, by algorithmic error, inability to capture salient features, failure to output results, etc.

Often, workflows are built around calculating a quantity of interest or preparing preliminary information to provide a foundation for calculating quantities of interest. Such preliminary information may include, for example, a geometric model. In some instances, quantities of interest are especially affected by geometry. For example, quantities of interest including air flow patterns and drag across the wing of an aircraft or exterior shell of an automobile are dependent on model geometry. However, geometries of models may have some uncertainty due, for example, to problems with images from which the models are made. For example, where the images are scans from medical imaging, problems with the images may include motion and registration artifacts, blooming artifacts, etc. Such uncertainty may impact computation of quantities of interest. Geometry sensitivity, then, may be defined as how much uncertainty in geometry may impact the computation of quantities of interest. In other words, sensitivity may describe the extent or amount to which geometry uncertainty affects a quantity of interest calculation.

Thus, a need exists for focusing attention on regions of a model that exhibit higher sensitivity, meaning greater impact on a quantity of interest contributed by uncertainty in geometry. These regions may be specific regions of an image where computations for quantities of interest may be sensitive to reconstructed geometry. A need exists for identifying regions of geometric models based on sensitivity and creating workflows that permit attention to and/or correction of these regions. More specifically, a need exists for guided workflows that may draw attention to highly sensitive regions in a model, for example, in the context of workflows guided by geometry sensitivity.

The foregoing general description and the following detailed description are exemplary and explanatory only and are not restrictive of the disclosure.

SUMMARY

According to certain aspects of the present disclosure, systems and methods are disclosed for guiding a workflow based on geometry sensitivity information. One method includes: determining a geometric model associated with a target object; determining one or more quantities of interest; determining sensitivity information associated with one or more subdivisions of the geometric model and the one or more quantities of interest; and generating, using a processor, a workflow based on the sensitivity information.

In accordance with another embodiment, a system for guiding a workflow, comprises: a data storage device storing instructions for guiding a workflow using geometry sensitivity information; and a processor configured for: determining a geometric model associated with a target object; determining one or more quantities of interest; determining sensitivity information associated with one or more subdivisions of the geometric model and the one or more quantities of interest; and generating, using a processor, a workflow based on the sensitivity information.

In accordance with yet another embodiment, a non-transitory computer readable medium for use on a computer system containing computer-executable programming instructions for performing a method of guiding a workflow based on geometry sensitivity information is provided. The method includes: determining a geometric model associated with a target object; determining one or more quantities of interest; determining sensitivity information associated with one or more subdivisions of the geometric model and the one or more quantities of interest; and generating, using a processor, a workflow based on the sensitivity information.

Another method includes: obtaining a geometric model associated with a target object; determining one or more parameters associated with the geometric model; determining sensitivity information associated with a sensitivity of one or more quantities of interest in relation to the one or more parameters; and altering, using a processor, a workflow for interacting with the geometric model based on the sensitivity information.

In accordance with another embodiment, a system for guiding a workflow, comprises: a data storage device storing instructions for guiding a workflow using geometry sensitivity information; and a processor configured for: obtaining a geometric model associated with a target object; determining one or more parameters associated with the geometric model; determining sensitivity information associated with a sensitivity of one or more quantities of interest in relation to the one or more parameters; and altering, using a processor, a workflow for interacting with the geometric model based on the sensitivity information.

In accordance with yet another embodiment, a non-transitory computer readable medium for use on a computer system containing computer-executable programming instructions for performing a method of guiding a workflow based on geometry sensitivity information is provided. The method includes: obtaining a geometric model associated with a target object; determining one or more parameters associated with the geometric model; determining sensitivity information associated with a sensitivity of one or more quantities of interest in relation to the one or more parameters; and altering, using a processor, a workflow for interacting with the geometric model based on the sensitivity information.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1:
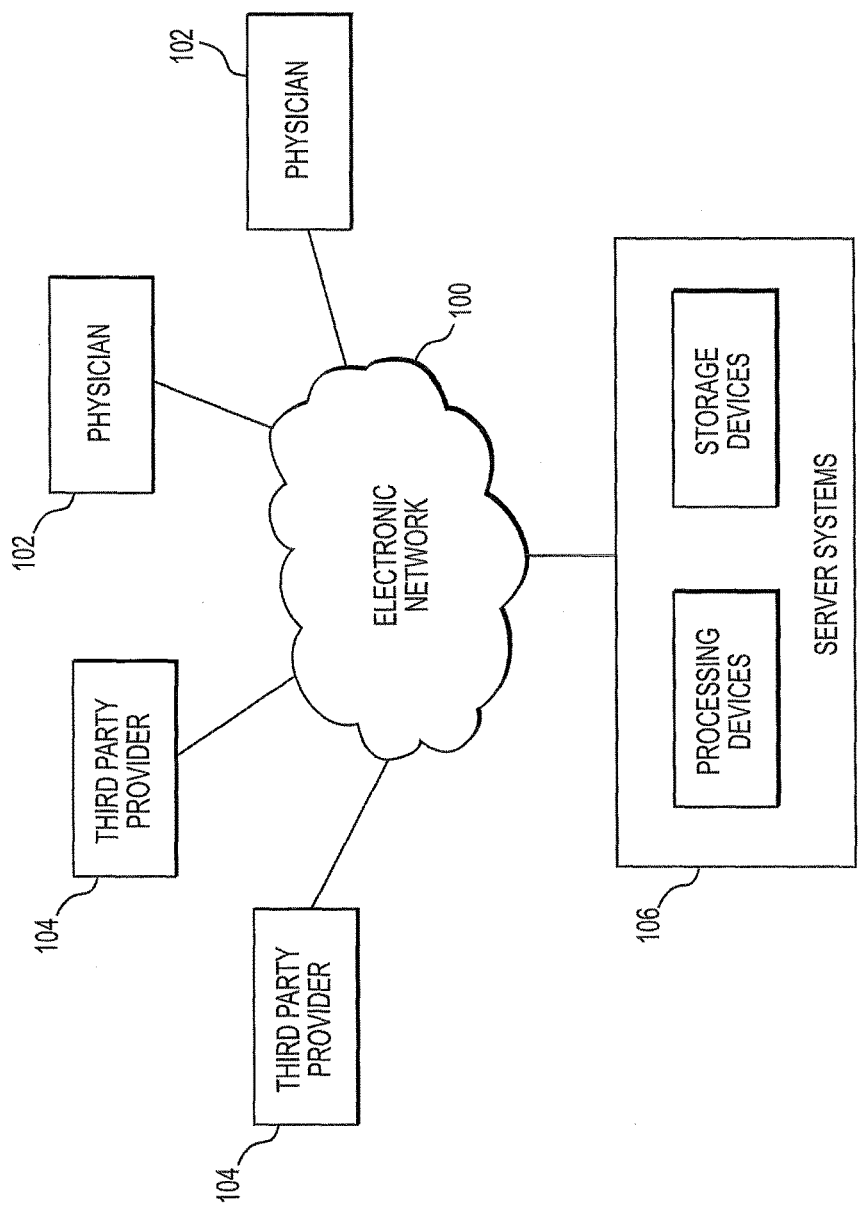
FIG. 1 is a block diagram of an exemplary system and network for using geometry sensitivity information to guide workflow, according to an exemplary embodiment of the present disclosure.

Reference will now be made in detail to the exemplary embodiments of the invention, examples of which are illustrated in the accompanying drawings. Wherever possible, the same reference numbers will be used throughout the drawings to refer to the same or like parts.

As described above, workflows may be involved in any automated or semi-automated process. Outputs from previous steps may be used as inputs in subsequent steps. Guided workflows may include a semi-automated process where manual corrections may be made to a workflow. In one embodiment, outputs of the workflow may be reprocessed and/or calculated based on corrections made in steps prior to calculating those outputs. At the same time, fidelity in modeling may be important. Acquiring an accurate model may ensure accuracy in quantities of interest computed based on the model.

In some instances, quantities of interest may be especially affected by geometry in a model. In other words, uncertainty of models, for example, due to motion and registration artifacts, blooming artifacts, etc. may impact computation of quantities of interest. Geometry sensitivity, then, may quantify the amount to which uncertainty in geometry impacts computing of quantities of interest.

Thus, in the context of guided workflows, a need exists for focusing attention on regions of a model that exhibit higher sensitivity. These regions may be specific regions of an image where calculations of quantities of interest may be sensitive or susceptible to geometry and/or uncertainty in geometry. A need exists for identifying regions of geometric models based on sensitivity, and creating workflows that permit attention to and/or correction of these regions.

The present disclosure is directed to a new approach of guiding or designing workflows. More specifically, the approach describes using geometry sensitivity information to guide workflow. The method may be applied to guide workflow where geometry may be important. In one embodiment, geometry may be estimated (e.g., from an image or scanner) or input directly. Such geometry may contain some degree of uncertainty. A quantity of interest may change in response to an input variable, where an exemplary input variable is related to geometric dimensions (e.g., uncertainty in diameter). The degree of this change and/or the rate of the change may be defined as, sensitivity. In other words, sensitivity may be defined as a rate of change in a quantity of interest relative to a unit change in an input variable.

The exemplary approach described includes guiding a workflow process based on geometry sensitivity, such as the degree to which uncertainty in geometry influences determinations of quantities of interest. For example, sensitivity information may be used to focus attention on particular regions of an image that may be sensitive to reconstructed geometry. Overall, the present disclosure is directed to a type of workflow process that may include one or more of the following steps: (i) receiving an input, such as raw, unprocessed data (e.g., imaging data), (ii) constructing a geometrical model using the input, (iii) filtering and processing the geometrical model to create one or more regions of interest, and (iv) performing computational analysis to calculate quantities of interest associated with one or more regions of interest. In one embodiment, the disclosure may focus on a step between (iii) and (iv), where some aspect of the model is computed to affect the workflow (e.g., guide user interaction with the model) before computational analysis is performed. Sensitivity to geometry may be an exemplary aspect of the model computed.

In some cases, geometry sensitivity may be defined as the standard deviation in a quantity of interest, due to uncertainty in the geometry. In some embodiments, geometry sensitivity information may help quantify the importance of a local geometry on one or more quantity of interest calculations. For example, sensitivity to geometry may be a useful metric in various applications, including quantifying uncertainty in air flow patterns and drag across the wing of an aircraft, optimizing shapes of automobiles to minimize draft and lift coefficients, computer-aided design (e.g., design of space vehicles, construction of buildings, design of bridges, design of prosthetics), reconstruction of organs and transport arteries from medical imaging data, etc. For medical imaging data, uncertainty in geometry may arise due to motion and registration artifacts, blooming artifacts, etc. In general, relationships between geometry and quantities of interest may be complex. For example, such relationships may be described by ordinary or partial differential equations. In some cases, calculating the impact of geometry on a quantity of interest may involve solving stochastic differential equations, which are computationally intensive and challenging to solve. In other cases, governing equations may be less complex. Even so, calculating sensitivity to geometry may be burdensome, involving steps including (i) parameterizing the geometry, (ii) reducing the continuous finite dimensional space of geometry to a finite dimensional subspace, and (iii) implementing efficient stochastic algorithms to quantify sensitivity.

The present disclosure is directed to facilitating the creation of accurate models, such as models in preparation for computational analysis. Specifically, the present disclosure may include forming accurate models by way of using geometry sensitivity information to make guided workflows directed to model creation. The present disclosure may include several methods for designing or directing workflows to focus attention on regions identified as having higher sensitivity and possibly requiring attention or correction. The method of the disclosure may be applied directly on parameterized or constrained geometries, for example, where geometric surfaces are constrained to be non-uniform rational B-spline (NURBS) surfaces.

Referring now to the figures, FIG. 1 depicts a block diagram of an exemplary system and network for using geometry sensitivity information to guide workflow. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
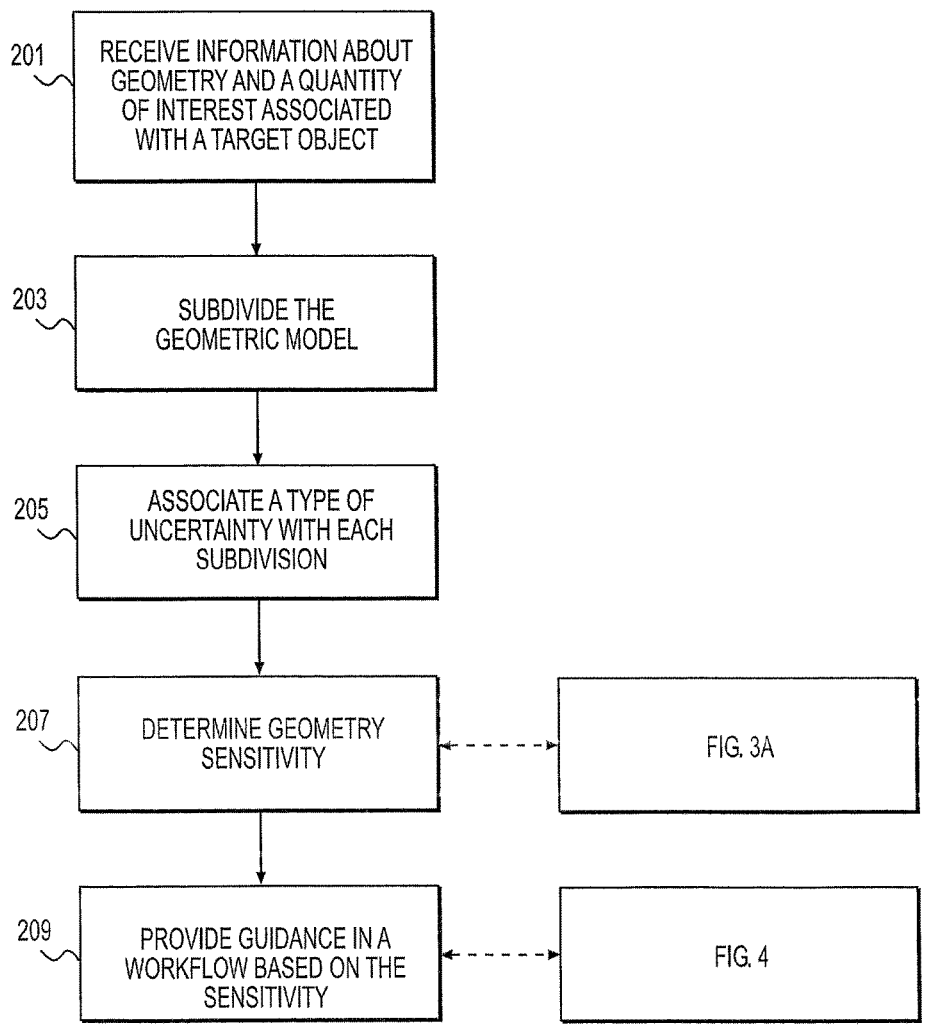
FIG. 2 is a block diagram of an exemplary method for using geometry sensitivity information for guiding workflow, according to an exemplary embodiment of the present disclosure.

FIG. 2 is a block diagram of an exemplary method 200 for using geometry sensitivity information for guiding workflow, according to an exemplary embodiment of the present disclosure. Method 200 may be performed by server systems 106, based on information, images, and data received from physicians 102 and/or third party providers 104 over electronic network 100. The method of FIG. 2 may include receiving information about a target object's geometry, as well as a quantity of interest related to the object geometry (step 201). For example, the input geometry of a target object may be specified analytically (e.g., Bezier splines in the form of implicit functions (e.g., level set functions)). Input geometry may also include or be derived from any variety of images, including raw images acquired from a scan from computed tomography, magnetic resonance images, ultrasound images, images from a 3-D scanner, etc. The input data may be used to create a digital representation of the geometry of the target object, including regions of interest. In one embodiment, the digital, geometric model representation of the target object may be extracted from the input information. For instance, geometry may be isolated and extracted from input images. The geometric model may be constructed using image intensity and gradient measures of the raw image, using prior knowledge and statistical methods, such as Bayesian, maximum likelihood estimates, manifold learning, and/or machine learning. In one instance, the quantity of interest may relate to geometries that may vary in time and space.

In one embodiment, the geometric model may then be subdivided so that each region may be mapped to a sensitivity value (step 203). Either each region may be considered a single independent random variable, or various geometric regions may have sensitivity values that are correlated to each other. In one embodiment, subdivisions may be equally spaced components, produced by splitting the geometry evenly. Alternately, geometric regions may be based on salient locations of the geometry.

In one embodiment, the next step may include determining some uncertainty measure associated with each subdivision (step 205). The uncertainty may be related to imaging modality acquisition protocol, reconstruction method, etc. For example, the measure may include the form and magnitude of uncertainty. Form of uncertainty may be based on probability distribution functions, the most common being Gaussian and Uniform distributions. Magnitude of uncertainty may include a magnitude of an uncertainty associated with an input used to calculate a quantity of interest. Using the embodiment previously described, magnitude may entail uncertainty in geometry, such as, specifically, geometry that may be used to calculate a quantity of interest. An appropriate magnitude of uncertainty may be assigned for each associated, selected sub-region. Sensitivity may then be an uncertainty in an output quantity of interest, calculated based on geometry input into the calculation of the quantity of interest.

In one embodiment, the next step may include determining the sensitivity value of the quantity of interest for each subdivision (step 207). In one embodiment, step 207 may include determining a functional relationship between a geometry and a quantity of interest. Step 207 may further include calculating the quantities of interest for a finite geometry (e.g., subdivision), then generating a histogram of the quantities of interest for that geometry. Step 207 may determine that a standard deviation calculated from the histogram is the sensitivity value assigned to each subdivision of the geometry, for a particular quantity of interest. Step 207 is described in further detail in FIG. 3A.

In one embodiment, the step afterwards may include providing user guidance (step 209) based on the sensitivity information. For example, a user may be guided to inspect subdivisions that have sensitivities above a certain threshold. In one embodiment, the user may be guided via a presentation in which the subdivisions with the greatest sensitivity are highlighted on a representation of the target object. Alternately or in addition, the internal workflow of the system may adjust to guide a user to inspect the most sensitive subdivisions. The size or resolution of subdivisions displayed for inspection may be dynamic. An exemplary method for determining resolution-based sizes of subdivision is disclosed, for example, in U.S. Provisional Application No. 61/948,325, filed Mar. 5, 2014, entitled "Method and System for Geometric Sensitivity Prediction Using Machine Learning," which is hereby incorporated by reference herein in its entirety.

In one embodiment, step 209 may include calculating the sensitivity ($\sigma_q$) for each geometric segment, then calculating the maximum $\sigma_q$ to determine a geometric segment where geometry may add the greatest uncertainty to a quantity of interest. Step 209 is described in further detail in FIG. 4.

Figure 3A:
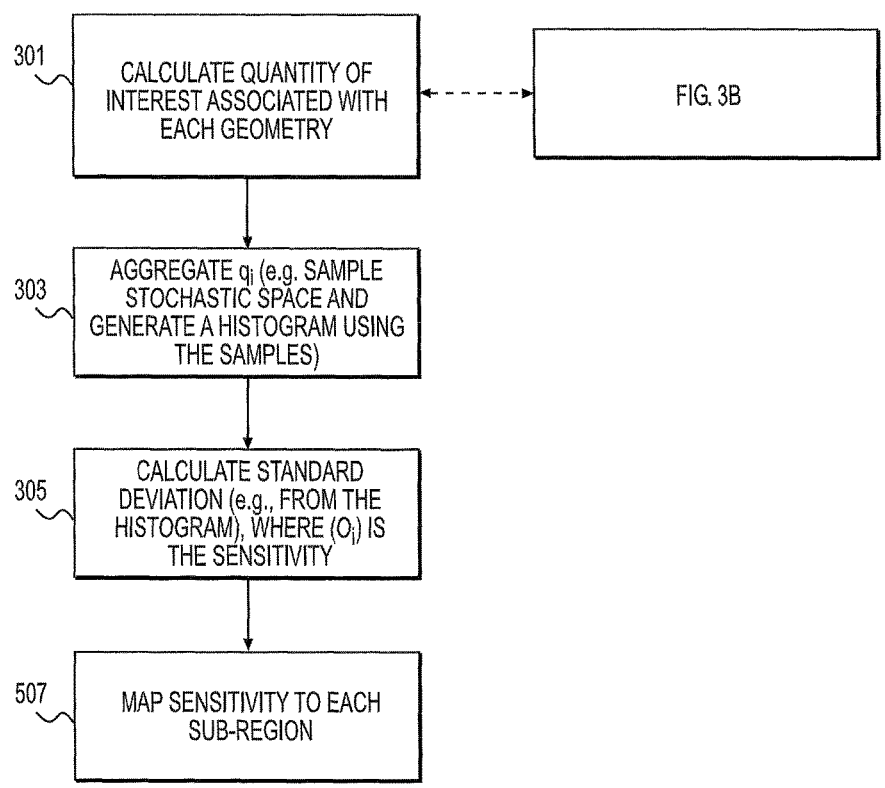
FIG. 3A is a block diagram of an exemplary method for determining the sensitivity of a quantity of interest for each subdivision, according to an exemplary embodiment of the present disclosure.

FIG. 3A is a block diagram of an exemplary method 300 for step 207 of determining the sensitivity of the quantity of interest for each subdivision, according to an exemplary embodiment of the present disclosure. Method 300 may be performed by server systems 106, based on information, images, and data received from physicians 102 and/or third party providers 104 over electronic network 100. Determining the sensitivity may serve to quantify the impact of the uncertainty set out in step 205 of method 200. Quantifying the impact of the uncertainty may help assess the functional significance of uncertainty in each geometric sub-region for a quantity of interest. To determine the sensitivity for each subdivision, method 300 may first include calculating, retrieving, or obtaining a quantity of interest (q) associated with each model and/or each geometry (step 301). For example, users may be interested in different quantities of interest, depending on a type of model evaluated. For instance, a quantity of interest of a model including a coronary vessel may include a coronary resistance, a flow, a pressure, a fractional flow reserve (FFR), etc. Thus, step 301 may include calculating values of the quantity of interest at one or more locations of the model and/or geometry, and the calculated values of the quantity of interest at any location of the model and/or geometry may be dependent on changes in or sensitivity of geometry at any of one or more of the identified subdivisions. Step 303 may include aggregating the $q_i$. For example, aggregation may be performed by sampling a stochastic space using an assigned probability distribution for each geometric parameter. Such aggregation may further include generating a histogram of the samples. Step 305 may include calculating a standard deviation based on the histogram from step 303, where the sensitivity ($\sigma_q$) may be the standard deviation assigned to each subdivision of the geometric item of interest. In one embodiment, step 300 may further include generating a map wherein sensitivity is mapped to each sub-region (step 307).

Figure 3B:
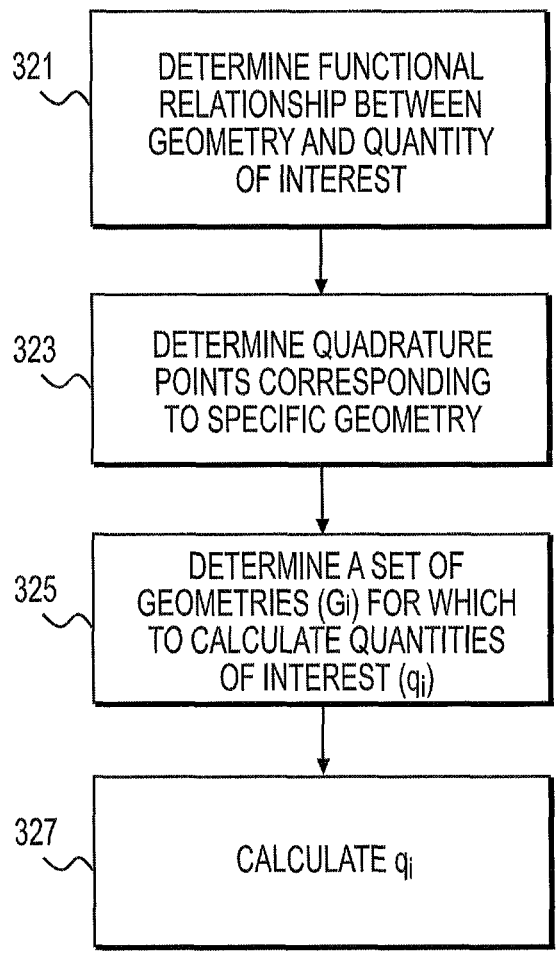
FIG. 3B is a block diagram of an exemplary method for calculating quantities of interest, according to an exemplary embodiment of the present disclosure.

FIG. 3B is a block diagram of an exemplary method 320 for calculating the $q_i$, according to an exemplary embodiment of the present disclosure. Method 320 may also be performed by server systems 106, based on information, images, and data received from physicians 102 and/or third party providers 104 over electronic network 100. First, method 320 may include determining a functional relationship between geometry (G) and a quantity of interest (q) (step 321). In one embodiment, geometry (G) may be geometry from the geometric model from steps 201 or 203. Furthermore, the functional relationship between geometry (G) and quantity of interest (q) may be a complex functional relationship, not trivial to obtain. In other words, step 321 may include finding a functional relationship, q=f(G). Next, quadrature points associated with a specific geometry (G) may be found (step 323). In one embodiment, the quadrature points may be found using a stochastic collocation algorithm, which may calculate q's at the quadrature points using, for example, the Smolyak sparse grid algorithm, where each quadrature point corresponds to a specific geometry. In one embodiment, step 325 may include determining or identifying a set of geometries ($G_i$). For example, $G_i$ may include a set of geometries for which $q_i=f(G_i)$ applies. In any case, step 325 may include determining a set of geometries ($G_i$) for which to calculate associated $q_i$. Consequently, step 327 may include calculating $q_i$ corresponding to $G_i$, for example, based on $q_i=f(G_i)$.

Figure 4:
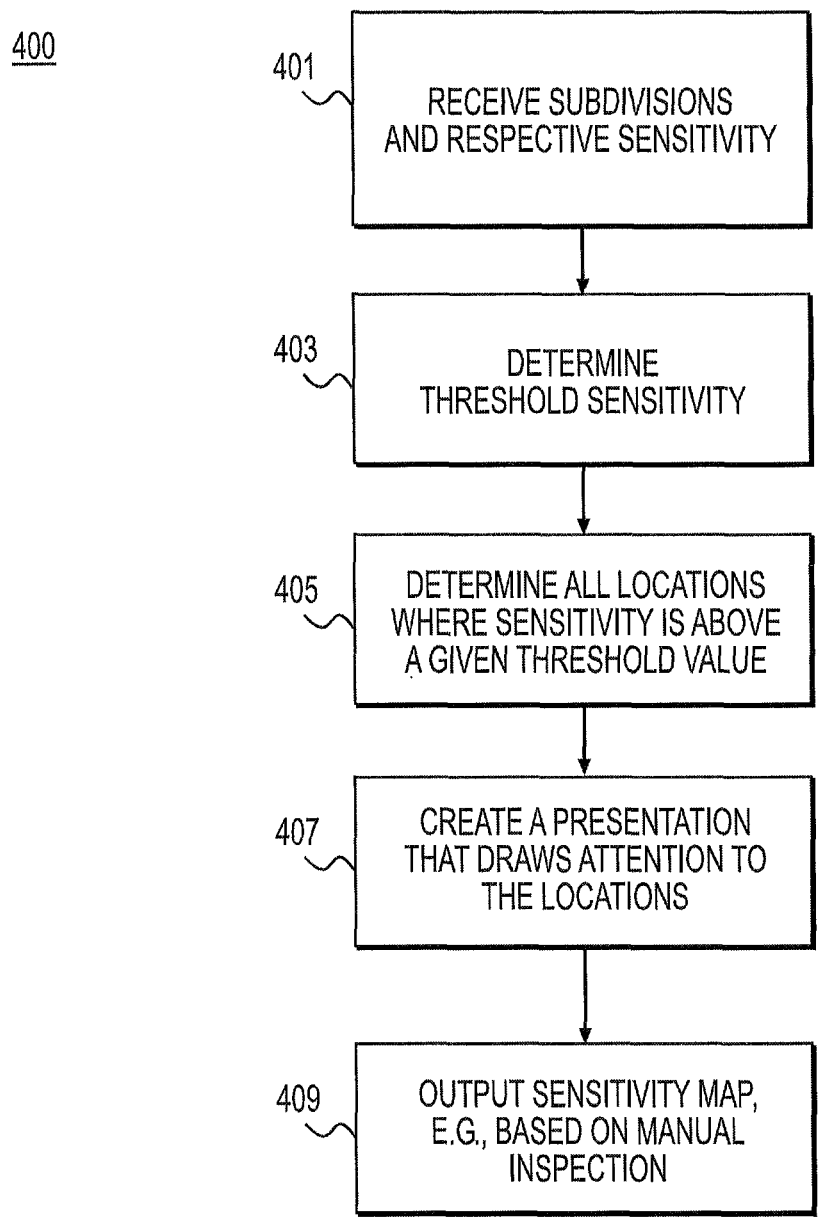
FIG. 4 is a block diagram of an exemplary method for guiding users to inspect subdivisions of a model, image, and/or geometry based on sensitivity, according to an exemplary embodiment of the present disclosure.

FIG. 4 is a block diagram of an exemplary method 400 for step 209 of guiding users to inspect subdivisions based on sensitivity, according to an exemplary embodiment of the present disclosure. Method 400 may be performed by server systems 106, based on information, images, and data received from physicians 102 and/or third party providers 104 over electronic network 100. In one embodiment, step 401 may include receiving sensitivity values for respective subdivisions, for example, as calculated by method 300. Step 403 may include determining a cutoff, or threshold, sensitivity value. Such a threshold may provide the basis for rendering a presentation of the model for inspection. In one embodiment, step 403 may include identifying one global cutoff for a geometric model, where sensitivity values may dictate whether a region or subdivision is highly sensitive. For example, sensitivity values above one threshold may result in a geometric region of one color, while sensitivity values above another threshold may correspond to a geometric region of another color.

In another, further embodiment, step 403 may include identifying multiple thresholds, each of varying sensitivity. For example, step 403 may include determining threshold values specific to subdivisions. For instance, threshold values may vary across various regions or subdivisions of a geometric model. In an exemplary case where a geometric model includes a model of coronary arteries, a threshold value for proximal regions may differ from a threshold value for distal regions. In addition, threshold values for secondary and/or tertiary vessels may be different from threshold values for main coronary arteries.

Step 405 may include determining all locations where sensitivity is above a threshold, for example, as determined in step 403. Furthermore, step 407 may determine a user interaction that draws attention to the locations noted in step 405. For example, one such user interaction may include highlighting or color-coding regions on a user-visible representation, where the colored regions are associated with respective sensitivity values. A user may know to inspect the highlighted and/or color-coded regions and ensure fidelity of geometry. Another example may include alternating a workflow of the system or sequence of steps to guide a user to inspect and/or prioritize more sensitive subdivisions. For instance, highly sensitive regions may be highlighted in a given color (e.g., red), throughout a workflow, as a user is inspecting the regions so that a user may track the region from view to view in a workflow. In one embodiment, the workflow sequence and/or coloring of the regions may change as a user inspects and/or interacts with regions. As a further example, step 407 may include identifying whether manual inspection is desired and generating user interaction channels that promote and guide the manual inspection. For example, step 407 may include determining conditions that may help identify a situation where manual inspection is desired. Then, step 407 may include prompts that require users to approve or alter an image prior to continuing in a workflow toward a completed, approved geometric model. Step 409 may further include outputting a sensitivity map based on the calculated sensitivity values' associations with locations in the geometric model. In one embodiment, the sensitivity map output by step 409 may include the user-visible representations for user inspection. In another embodiment, a sensitivity map may also include a final sensitivity map, after user inspection and approval.

Figure 5A:
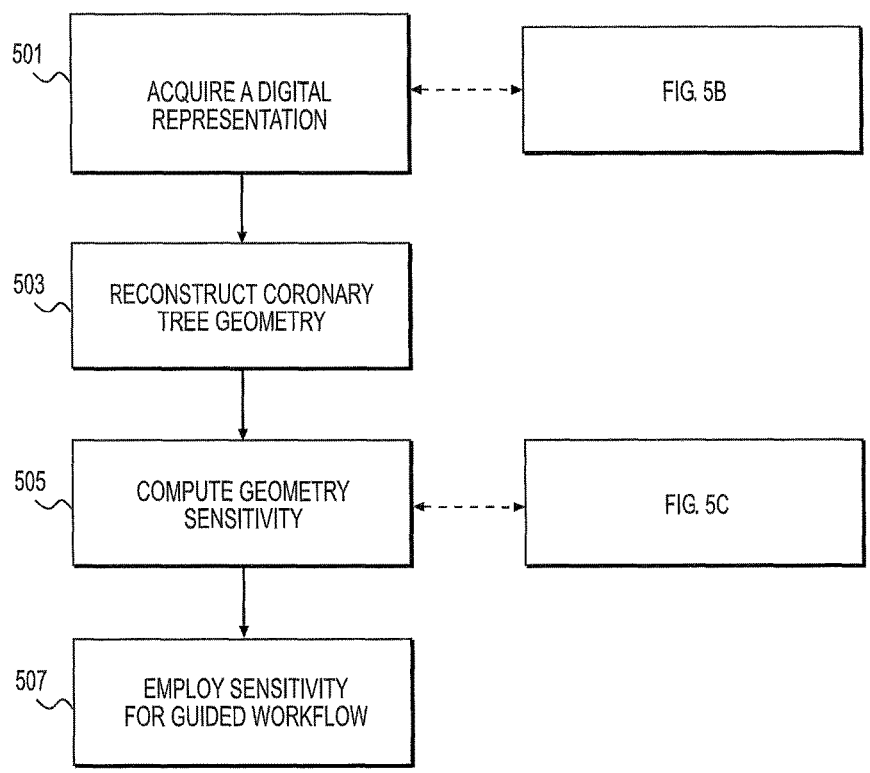
FIGS. 5A-5C are block diagrams of a specific embodiment of using geometry sensitivity information for guiding workflow for a coronary model, according to an exemplary embodiment.
Figure 5B:
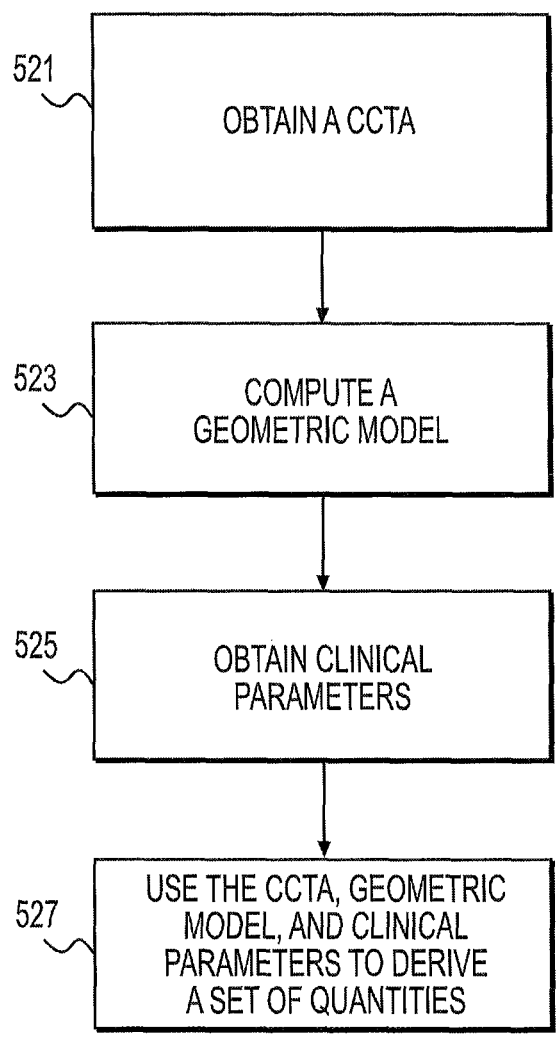
Figure 5C:
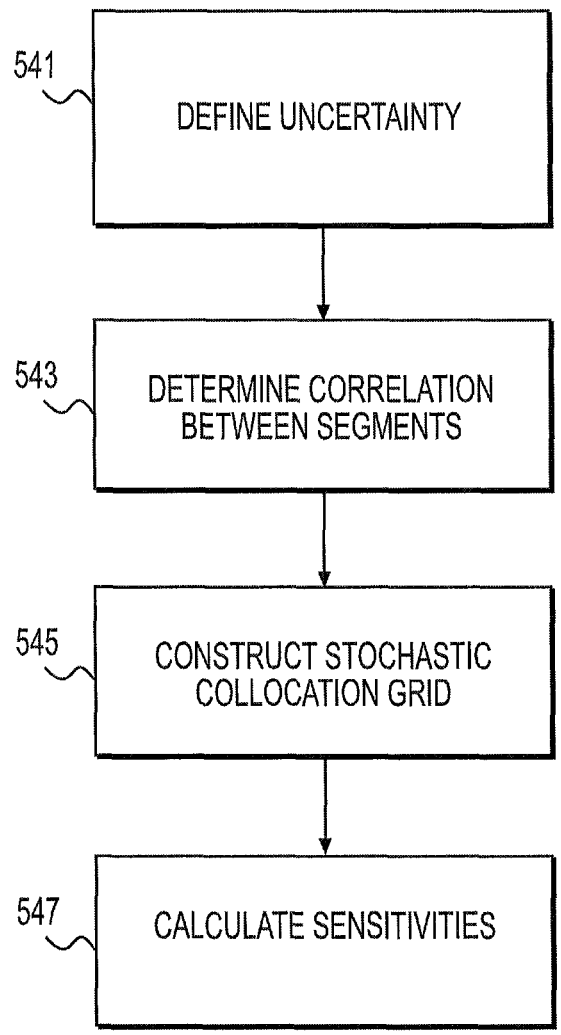

FIGS. 5A-5C are block diagrams of a specific embodiment of method 200 of using geometry sensitivity information for guiding workflow, according to an exemplary embodiment. Methods 500-540 may be performed by server systems 106, based on information, images, and data received from physicians 102 and/or third party providers 104 over electronic network 100. The specific embodiment, method 500, describes application of method 200 to a technique of calculating sensitivity of fractional flow reserve to geometry information for performing patient-specific estimation. Such a technique may be especially useful for patients with heart disease. In one embodiment, step 501 may include acquiring a digital representation of various patient information. In the case of a patient suspected of having coronary disease, step 501 may include determining desired patient information and obtaining the medical images, clinical information, and/or patient-specific measurements desired for subsequent steps. Various embodiments of such a method and system of computing a geometric model to noninvasively determine information relating to blood flow is described in greater detail in U.S. Pat. No. 8,315,812, filed Jan. 25, 2011, and entitled "Method and System for Patient-Specific Modeling of Blood Flow," which is hereby incorporated by reference in its entirety. Further detail of an embodiment of step 501 is provided in FIG. 5B.

After collecting desired information, step 503 may include reconstructing coronary tree geometry for a geometric model of a target object. Step 503 may be achieved through any reconstruction method, including ostia detection, centerline path reconstruction, reconstruction of vessel lumen, trimming vessels, etc. Ostia detection may include identifying, for a patient, locations where coronary arteries originate from the aorta, meaning one or more ostium. Vessels near ostia may be critical for transporting oxygenating blood from the aorta to the entire coronary tree, so identifying each ostium and the location of each ostium may be critical in performing coronary related simulations. A machine learning method, along with an understanding of the unique bifurcation pattern at the ostia, may be used to automatically detect location of ostia.

Centerline path reconstruction may include generally identifying the structure of coronary arteries. Centerlines may be fictional path lines that pass inside coronary arteries. They may be useful in estimating the number and location of bifurcations, and when taken collectively, centerlines may help form reconstructions of coronary artery geometry. Centerline paths may be reconstructed automatically or semi-automatically, and centerline paths may be reconstructed using connectivity of a contrast agent in a vessel lumen, by fitting models of shape and appearance to image data, using region growing techniques and connected component analysis, by employing optimization using vesselness measures, etc.

Reconstruction of a vessel lumen may include incorporating the location of centerlines, along with raw image(s) of pixel intensities and machine learning algorithm(s) trained on a database of images with a ground truth lumen. The reconstruction of a vessel lumen may include associating probabilities for a finite set of candidate lumens, where a reconstruction of a vessel lumen is based on a maximum likelihood estimate that a candidate lumen, in fact, portrays a lumen of interest. Reconstructions involving trimming vessels may be taken into account since a location of trimming may affect a resultant coronary tree geometry of interest, as well as associated quantities of interest and sensitivity measures. Trimming, or truncating, geometry and modeling the micro-vessels and capillary arteries using lumped parameters that depend on trim plane location, means that trimming may impact a geometric model and quantity of interest computed from the model. In the present embodiment where a quantity of interest is focused on what is traveling through the micro-vessels and arteries, it may be preferable for a geometric model (and associated quantity of interest) to not be highly sensitive to trim location. In this context, a fractional flow reserve (FFR) is the quantity of interest. Since FFR concerns geometry inside of a lumen, less precise trimming may be computed even if trimming is not as precise.

In one embodiment, step 505 may include computing geometry sensitivity. In one embodiment, step 505 may include identifying or defining uncertainty, such as, uncertainty arising from imaging artifacts or reconstruction algorithms, for instance. Next, step 505 may include determining associations between geometries that may allow for sensitivity information to apply across a region of a geometry or be isolated to a particular segment in geometry. Step 505 may further include constructing a stochastic collocation grid for a geometric object, and then calculating a quantity of interest for each stochastic collocation point within the stochastic collocation grid. Once the quantity of interest is calculated, the standard deviation and confidence intervals of the quantity of interest may be found. That calculated standard deviation may constitute the sensitivity. Further detail of step 505 is provided in FIG. 5C.

Lastly, step 507 may include using the sensitivity for a guided workflow. Step 507 is an exemplary application of step 209 and corresponding exemplary method 400. In one embodiment for step 507, sensitivity information may guide geometry construction. For example, step 507 may include assigning a threshold (e.g., a value of 0.05) after sensitivity information is calculated. In one embodiment, step 507 may include highlighting regions within a coronary tree that have sensitivity values higher than the threshold. A representation including highlighted and non-highlighted regions may be presented to a reviewer. In one instance, a reviewer may be directed to inspect highlighted regions to ensure fidelity, for example, of both a reconstructed model and location of trimming planes as given from reconstruction(s) of step 502. As previously discussed, step 507 may also include determining multiple thresholds or ranges of thresholds so that there may be various colored regions, each depicting some range or level of sensitivity.

Step 507 may further include prompting a manual correction step to reinstate a lumen to a desired size and shape. The new geometry may affect sensitivity values, so this aspect of step 507 may trigger repeating of step 505 to recalculate sensitivity. Alternatively or in addition to highlighting, step 507 may include guiding a reviewer through a series of views in a software program to inspect areas of high sensitivity. In a further embodiment, sensitivities may be saved to an electronic storage medium to guide future workflows or to resume an interrupted workflow. The steps of determining geometry and ensuring fidelity of geometry may serve as a precursor to calculating quantities of interest.

FIG. 5B is a block diagram of an exemplary method 520 for acquiring a digital representation of various patient information, according to an exemplary embodiment. Method 520 may be a process of acquiring patient data needed to form the geometry associated with a quantity of interest. Accurately forming the geometry may allow the overall method 500 to accurately determine sensitivity, thus quantifying the degree to which variability in a quantity of interest measurement is attributable to geometry. In one embodiment, step 521 may include obtaining a cardiac computed tomography angiography (CCTA) image. However, step 521 may include acquiring any medical images of a patient. In one embodiment, step 523 may include computing a geometric model based on the CCTA or other medical images from step 521. For instance, step 523 may include computing a geometric model of all the vessels of interest, including ascending aorta, left/right coronary artery, left circumflex artery, left obtuse marginal, and any other visible vessels of interest. In an exemplary embodiment, a method and system determines information relating to blood flow in a specific patient using information retrieved from the patient noninvasively.

Step 525 may include obtaining clinical parameters. For example, a set of clinical parameters obtained in step 525 may include measurements for heart rate, systolic and diastolic brachial blood pressures, hematocrit, patient height and weight, and patient history (e.g., smoking status, presence/absence of diabetes, etc.).

Step 527 may include calculating quantities based on step 521 and step 525. The derived quantities may include myocardial mass, body surface area, viscosity, inlet aortic flow rate, coronary flow rate, coronary resistance, and resistance of outlet aorta. Myocardial mass ($m_{myo}$) may be obtained using image segmentation of the left ventricle. For example, the segmentation may help calculate the volume of myocardium, which may be multiplied with a density (usually assumed to be constant at ~1.05 g/cm$^3$). Body surface area may be calculated from patient height (h) and weight (w) as $$BSA = \sqrt{\frac{hw}{3600}}.$$

Viscosity may be calculated from hematocrit (hem) as $$\eta = \frac{c}{\left(1 - \frac{hem}{100} \div\right)^{2.5}},$$

where c may be taken as 0.0012. Inlet aortic flow rate (Q) may be calculated from scaling studies as $$Q = \frac{1}{60} BSA^{1.15}.$$

In one example, coronary flow rate ($q_{cor}$) may be calculated from myocardial mass as $$q_{cor} = c_{dil} \frac{5.09}{60} m_{myo}^{0.75},$$

where $c_{dil}$ may denote the dilation factor. Coronary resistance may include calculating a net coronary resistance from the desired coronary flow. Resistance value for individual outlets may be calculated based on areas of the respective outlets. Resistance of the outlet aorta may be calculated based on aortic pressure, aortic flow rate, and desired coronary flow rate. Obtaining all the values from steps 521-527 may provide the basis for reconstructing coronary tree geometry (step 503).

FIG. 5C is a block diagram of an exemplary method 540 for computing geometry sensitivity, according to an exemplary embodiment. Method 540 may be one possible embodiment of performing step 505 for determining geometry sensitivity. In one embodiment, step 541 may include defining uncertainty in geometry. For example, various reconstructions or geometries from step 502 (or related steps 201 and 203 from general method 200) may be associated with different types of uncertainties. For example, a reconstruction of a vessel lumen (as described for step 503 of method 500) may be considered a statistical realization over a possible range of geometries. In other words, the model of vessel lumen geometry from step 503 may be an estimate based on various geometries. The reconstruction may be an approximation, over a possible range of geometries, of a patient's actual vessel lumen. Such an uncertainty may arise from image noise, artifacts, or the reconstruction algorithm used for step 503. In one embodiment, step 541 may include determining a probability distribution assigned to a family of geometries, within which a "true geometry" may lie. Such a distribution may be data-driven, or a Gaussian or Uniform distribution.

Step 543 may include determining one or more correlations between subdivisions or segments of geometry. For example, step 543 may include splitting patient-specific geometry (from step 503) into regions. Continuing from the example of a reconstruction of a vessel lumen, step 543 may include splitting the patient-specific geometry (e.g., the reconstruction) into regions based on bifurcation locations. Any segment between two bifurcations, ostium and bifurcation, and/or ostium and trimmed outlet node may be mapped as an independent random variable. This may mean uncertainty in geometry within a segment may be fully correlated, and uncertainty across segments may be uncorrelated. In one instance, step 543 may further include determining subdivisions of geometry based on sensitivity. For example, if sensitivity of a segment is deemed higher than a threshold value, step 543 may include dividing the segment further into two equal segments, which are designated to be uncorrelated (e.g., independent random variables). From there, step 543 may prompt resuming the sensitivity analysis. In one case, sensitivity analysis may be terminated when either (i) there are no segments whose sensitivities are above a threshold value, or (ii) segments cannot be split anymore (e.g., as governed by resolution of centerline points. In one embodiment, the situation (i) of no segments being associated with sensitivities above a threshold value may cause, for instance, a prompt to retrieve more input images and/or resetting of output values.

Step 545 may include constructing a stochastic collocation grid in order to calculate a quantity of interest with respect to geometries within the family of geometries and estimate solutions for geometries outside of the family of geometries. For example, interpolation may be used to estimate solutions. For each independent segment, the set of possible geometries may be infinite (e.g., due to continuous probability distributions). First, then, step 545 may include mapping the infinite set of possible geometries to a finite number. The finite set of possible geometries may comprise a probability set, where solutions corresponding to any other geometry in the probability set (e.g., solutions outside the finite set or outside the family of geometries) may be obtained using interpolation in a stochastic space. In one case, a Smolyak sparse grid algorithm may be used to identify a set of collocation points, where each point may correspond to a unique geometry. The algorithm may be repeated for each geometric segment identified, for example, in step 543.

Step 547 may include calculating sensitivities. For example, the quantity of interest for method 500 may be Fractional Flow Reserve (FFR), which may be the ratio of local to aortic pressure or local to aortic flow. In one embodiment, FFR may be computed at each stochastic collocation point. Once FFR is calculated for various uncertainties, step 547 may include constructing a stochastic space representation of FFR. For example, step 547 may include calculating FFR for all sources of uncertainties identified in step 541, at each collocation point. The stochastic space representation of FFR may then be a representation based on all the uncertainties determined from step 541. In other instances, the representation may be based on a subset of the uncertainties. In one embodiment, the stochastic space may be sampled to calculate standard deviation and confidence intervals of FFR. Sensitivity may be defined as the standard deviation of FFR. Calculating the standard deviation of FFR may thus mean calculating the sensitivity. In one case, a machine learning algorithm may be used to calculate FFR for the numerous geometric segments and stochastic collocation points. In another case, blood flow simulations may be used to calculate FFR. The blood flow simulations for calculating FFR may be more suitable for cases with fewer geometric segments or stochastic collocation points. Various embodiments of such a method and system for determining uncertainty related to quantities of interest are described in greater detail in U.S. Nonprovisional application Ser. No. 13/864,996 entitled "Method and System for Sensitivity Analysis in Modeling Blood Flow Characteristics," filed Apr. 17, 2013, the entire disclosure of which is hereby incorporated by reference in its entirety.

Figure 6:
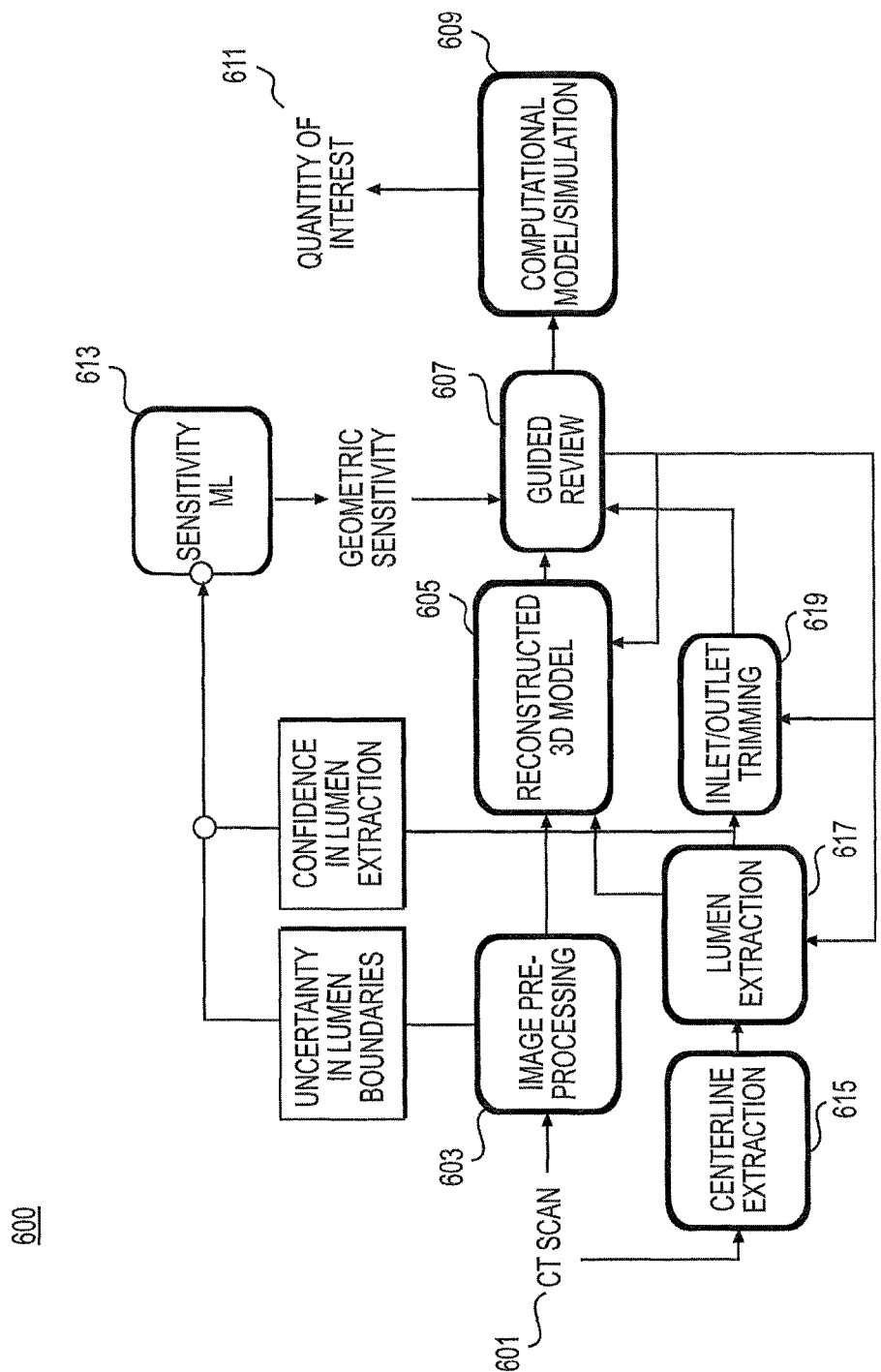
FIG. 6 is a block diagram of an exemplary method of a workflow process guided using sensitivity information, according to an exemplary embodiment.

FIG. 6 is a block diagram of an exemplary method 600 of a workflow process guided using sensitivity information, according to an exemplary embodiment. In one embodiment, step 601 may include obtaining images for a geometric model, for example, computed tomography (CT) scans. The scans may undergo image pre-processing (step 603), where the processed images may then be used for a 3-D model reconstruction (step 605). This model may be evaluated through a guided review, where accuracy of the model may be verified (step 607). Lastly, a verified model from step 607 may serve as a computational model and/or basis for simulations (step 609). The computations and simulations may produce quantities of interest (step 611). In one embodiment, pre-processing may include determination of uncertainty in lumen boundaries and/or determination of confidence in lumen extraction, which may then require inlet or outlet trimming. Based on the pre-processing, sensitivity may be determined (step 613), where sensitivity may specifically be geometry sensitivity. This sensitivity information may inform guided review (step 607), computations and simulations (step 609), and determinations of quantities of interest (step 611). In addition, images for a geometric model may undergo centerline extraction (step 615), lumen extraction (step 617), and/or inlet/outlet trimming (step 619) in preparation for creating the 3-D model of step 605. In one embodiment, guided review (step 607) may repeat steps 617 and 619 of lumen extraction and inlet/outlet trimming based on user input and/or newly received information.

Figure 7:
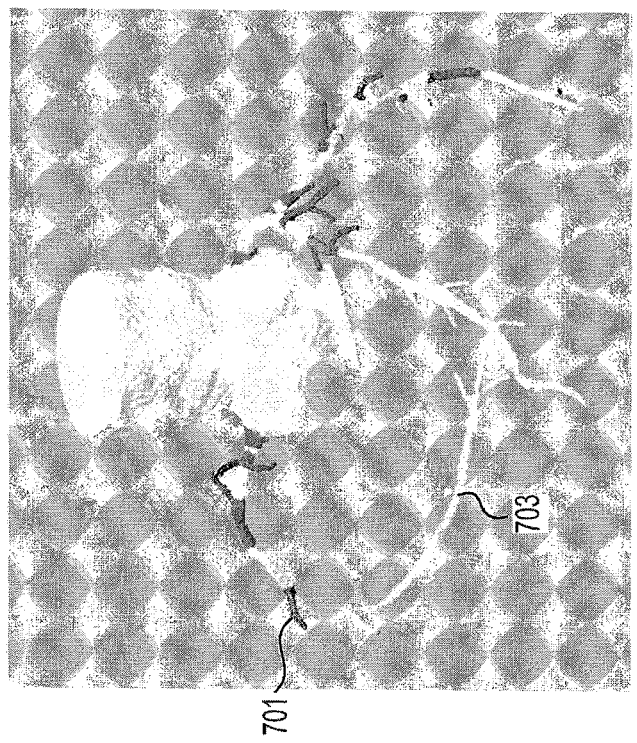
FIG. 7 is a diagram of an exemplary user interface that a user may view as part of a guided workflow, according to an exemplary embodiment.

FIG. 7 is a diagram of an exemplary user interface 700 that a user may see as part of a guided workflow, according to an exemplary embodiment. In one embodiment, darker regions 701 may denote regions where sensitivity values exceed a threshold value for sensitivity. Lighter regions 703 may show geometric regions where sensitivity values fall below the threshold. In this instance, a user may be prompted to examine each of the darker regions 701 more carefully. Alternately or additionally, a user may be informed of a sensitivity value, such as when the user moves, touches, points to, clicks on, or hovers a mouse over parts of the user interface 700. A user may take this sensitivity value into account to decide whether to rely on computed quantities of interest.

In summary, workflows may be guided based on various criteria. In simulations and computations using geometric models, quantities of interest may be susceptible to uncertainty, the degree of which is attributable to geometry (i.e., "geometry sensitivity," may assist in understanding how much a calculation for a quantity of interest may be affected by geometry). Thus, the presently disclosed method enables determining geometry sensitivity for the purpose of using the geometry sensitivity information to guide workflows.

Figure 8:
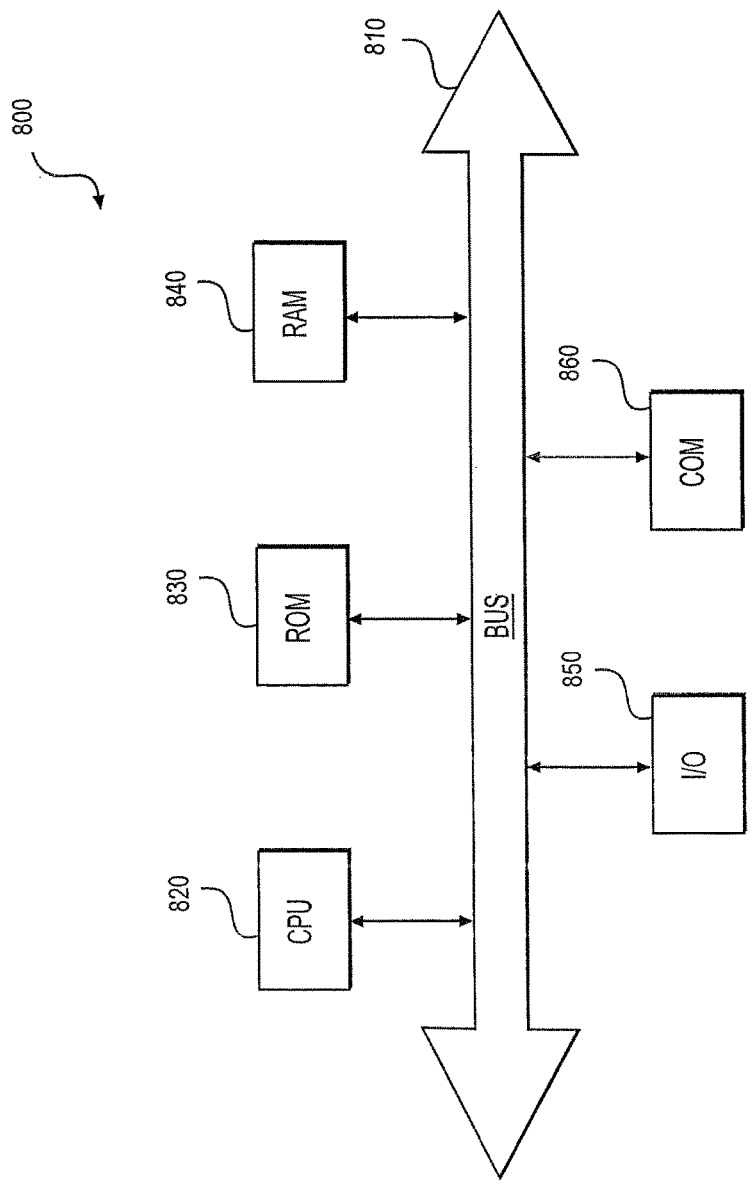
FIG. 8 is a simplified block diagram of an exemplary computer system in which embodiments of the present disclosure may be implemented.

FIG. 8 is a simplified block diagram of an exemplary computer system 800 in which embodiments of the present disclosure may be implemented, for example as any of the physician devices or servers 102, third party devices or servers 104, and server systems 106. A platform for a server 800, for example, may include a data communication interface for packet data communication 860. The platform may also include a central processing unit (CPU) 820, in the form of one or more processors, for executing program instructions. The platform typically includes an internal communication bus 810, program storage and data storage for various data files to be processed and/or communicated by the platform such as ROM 830 and RAM 840, although the server 800 often receives programming and data via a communications network (not shown). The hardware elements, operating systems and programming languages of such equipment are conventional in nature, and it is presumed that those skilled in the art are adequately familiar therewith. The server 800 also may include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

As described above, the computer system 800 may include any type or combination of computing systems, such as handheld devices, personal computers, servers, clustered computing machines, and/or cloud computing systems. In one embodiment, the computer system 800 may be an assembly of hardware, including a memory, a central processing unit ("CPU"), and/or optionally a user interface. The memory may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. The CPU may include one or more processors for processing data according to instructions stored in the memory. The functions of the processor may be provided by a single dedicated processor or by a plurality of processors. Moreover, the processor may include, without limitation, digital signal processor (DSP) hardware, or any other hardware capable of executing software. The user interface may include any type or combination of input/output devices, such as a display monitor, touchpad, touchscreen, microphone, camera, keyboard, and/or mouse.

Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to non-transitory, tangible "storage" media, terms, such as computer or machine "readable medium" refer to any medium that participates in providing instructions to a processor for execution.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of inspecting a geometric model, using a computer system, the method comprising: receiving (1) a geometric model of a target object and geometric parameters that define the geometry of the geometric model; and (2) a type of a quantity of interest that can be calculated for various points in the geometric model; calculating a first value of the quantity of interest corresponding to a first point of the geometric model; calculating a first sensitivity value of the first point, the first sensitivity value comprising a variability measure of the calculated first quantity of interest in response to changes in one or more values of the geometric parameters at the first point of the geometric model; calculating a second value of the quantity of interest corresponding to a second point of the geometric model, the second point being different from the first point; calculating a second sensitivity value, the second sensitivity value comprising a variability measure of the calculated second quantity of interest in response to changes in the one or more values of the geometric parameters at the second point of the geometric model; and if the first sensitivity value is higher than the second sensitivity value, generating, a display of the first point of the geometric model prior to a display of the second point of the geometric model, and if the second sensitivity value is higher than the first sensitivity value, generating a display of the second point of the geometric model prior to a display of the first point of the geometric model, wherein the displays are presented to a user for inspection of the geometric model and where a final geometric model is generated by reconstructing the geometric model based on a user response to at least one of the displays.

2. The method of claim 1, further including:
determining a workflow sequence including displays of one or more points of the geometric model, wherein the order of first displaying the first point or the second point is part of the workflow sequence.

3. The method of claim 2, wherein the workflow sequence include one or more representations, user prompts, workflow steps, or a combination thereof, wherein the one or more representations include highlighting a point of the geometric model based on a sensitivity value corresponding to the point of the geometric model.

4. The method of claim, further including:
determining a threshold value of sensitivity of the quantity of interest to the geometry of the geometric model.

5. The method of claim 4, further including:
determining sensitivity values corresponding to one or more additional points of the geometric model;
determining visible representations particular to points of the geometric model with corresponding sensitivity values that exceed the threshold value of sensitivity.

6. The method of claim 2, further including:
determining one or more conditions for manual inspection associated with the geometric model; and
determining the workflow sequence based on the one or more conditions for manual inspection.

7. The method of claim 2, further including:
determining one or more user corrections associated with the geometric model; and
determining the workflow sequence based on the one or more user corrections.

8. A system of inspecting a geometric model, the system comprising: a data storage device storing instructions for inspecting a geometric model; and a processor configured to execute the instructions to perform a method including: receiving (1) a geometric model of a target object and geometric parameters that define the geometry of the geometric model; and (2) a type of a quantity of interest that can be calculated for various points in the geometric model; calculating a first value of the quantity of interest corresponding to a first point of the geometric model; calculating a first sensitivity value of first point, the first sensitivity value comprising a variability measure of the calculated first quantity of interest in response to changes in one or more values of the geometric parameters at the first point of the geometric model; calculating a second value of the quantity of interest corresponding to a second point of the geometric model, the second point being different from the first point; calculating a second sensitivity value, the second sensitivity value comprising a variability measure of the calculated second quantity of interest in response to changes in the one or more values of the geometric parameters at the second point of the geometric model; and if the first sensitivity value is higher than the second sensitivity value, generating, a display of the first point of the geometric model prior to a display of the second point of the geometric model, and if the second sensitivity value is higher than the first sensitivity value, generating a display of the second point of the geometric model prior to a display of the first point of the geometric model, wherein the displays are presented to a user for inspection of the geometric model and where a final geometric model is generated by reconstructing the geometric model based on a user response to at least one of the displays.

9. The system of claim 8, wherein the processor is further configured for:
determining a workflow sequence including displays of one or more points of the geometric model, wherein the order of first displaying the first point or the second point is part of the workflow sequence.

10. The system of claim 9, wherein the workflow sequence includes one or more representations, user prompts, workflow steps, or a combination thereof, wherein the one or more representations include highlighting a point of the geometric model based on a sensitivity value corresponding to the point of the geometric model.

11. The system of claim 8, wherein the processor is further configured for:
a threshold value of sensitivity of the quantity of interest to the geometry of the geometric model.

12. The system of claim 11, wherein the processor is further configured for:
determining sensitivity values corresponding to one or more additional points of the geometric model;
determining visible representations particular to points of the geometric model with corresponding sensitivity values that exceed the threshold value of sensitivity.

13. The system of claim 8, wherein the processor is further configured for:
determining one or more conditions for manual inspection associated with the geometric model; and
determining the workflow sequence based on the one or more conditions for manual inspection.

14. The system of claim 8, wherein the processor is further configured for:
determining one or more user corrections associated with the geometric model; and
determining the workflow sequence based on the one or more user corrections.

15. A non-transitory computer readable medium for use on a computer system containing computer-executable programming instructions for inspecting a geometric model, the method comprising: receiving (1) a geometric model of a target object and geometric parameters that define the geometry of the geometric model; and (2) a type of a quantity of interest that can be calculated for various points in the geometric model; calculating a first value of the quantity of interest corresponding to a first point of the geometric model; calculating a first sensitivity value of the first point, the first sensitivity value comprising a variability measure of the calculated one or more values of the first quantity of interest in response to changes in one or more values of the geometric parameters at the first point of the geometric model; calculating a second value of the quantity of interest corresponding to a second point of the geometric model, the second point being different from the first point; calculating a second sensitivity value, the second sensitivity value comprising a variability measure of the calculated second quantity of interest in response to changes in the one or more values of the geometric parameters at the second point of the geometric model; and if the first sensitivity value is higher than the second sensitivity value, generating, a display of the first point of the geometric model prior to a display of the second point of the geometric model, and if the second sensitivity value is higher than the first sensitivity value, generating a display of the second point of the geometric model prior to a display of the first point of the geometric model, wherein the displays are presented to a user for inspection of the geometric model and where a final geometric model is generated by reconstructing the geometric model based on a user response to at least one of the displays.

16. The non-transitory computer readable medium of claim 15, the method further comprising:
determining a workflow sequence including displays of one or more points of the geometric model, wherein the order of first displaying the first point or the second point is part of the workflow sequence.

17. The non-transitory computer readable medium of claim 16, wherein the workflow sequence include one or more representations, user prompts, workflow steps, or a combination thereof,
wherein the one or more representations include highlighting a point of the geometric model based on a sensitivity value corresponding to the point of the geometric model.

* * * * *